United States Patent [19]

Grimes et al.

[11] Patent Number: 4,459,226

[45] Date of Patent: Jul. 10, 1984

[54] PROCESS FOR RECOVERING INSULIN

[75] Inventors: Denise L. Grimes; C. Stephen Hollinden, both of Indianapolis, Ind.

[73] Assignee: Eli Lilly and Company, Indianapolis, Ind.

[21] Appl. No.: 352,725

[22] Filed: Feb. 26, 1982

[51] Int. Cl.³ .......................................... C07C 103/52
[52] U.S. Cl. .................................................. 260/112.7
[58] Field of Search ...................................... 260/112.7

[56] References Cited

U.S. PATENT DOCUMENTS

| | | | |
|---|---|---|---|
| 3,069,323 | 12/1962 | Volini et al. | 167/75 |
| 3,221,008 | 11/1965 | Wolf et al. | 260/210 |
| 3,468,870 | 9/1969 | Smith et al. | 260/112.7 |
| 3,876,623 | 4/1975 | Jackson | 260/112.7 |
| 3,878,186 | 4/1975 | Jackson | 260/112.7 |
| 3,907,676 | 9/1975 | Jorgensen | 210/31 C |
| 4,129,560 | 12/1978 | Zoltobrocki | 260/112 R |
| 4,183,849 | 1/1980 | Hansen et al. | 260/112.7 |

FOREIGN PATENT DOCUMENTS

| | | |
|---|---|---|
| 850387 | 2/1977 | Belgium . |
| 2212695 | 9/1973 | Fed. Rep. of Germany . |
| 2600971 | 7/1976 | Fed. Rep. of Germany . |
| 6492/63 | 9/1960 | Japan . |
| 797959 | 7/1958 | United Kingdom . |
| 1054523 | 1/1966 | United Kingdom . |

*Primary Examiner*—Frederick E. Waddell
*Attorney, Agent, or Firm*—William C. Martens; Arthur R. Whale

[57] ABSTRACT

Insulin can be recovered for processing and re-use from an insulin-protamine complex by bringing the complex into contact with an aqueous medium having a pH of from about 2 to about 5 and containing an insulin dissociating or depolymerizing agent, a cation exchanger, and a salt at a concentration of from about 0.1 M to about 0.6 M.

9 Claims, No Drawings

PROCESS FOR RECOVERING INSULIN

BACKGROUND OF THE INVENTION

In the development of insulin formulations suitable for treatment of diabetes mellitus, it became desirable to alter the characteristics of insulin to prolong its blood-sugar-lowering effect. It was discovered that this could be achieved by conversion of the insulin to a complex which was only partly soluble at the pH of body fluids but which, over an extended period of time, would dissociate with release of insulin. The result is much less rapid insulin absorption.

When insulin is mixed with a properly buffered solution containing protamine, a protamine-insulin precipitate results which has poor solubility and therefore is only slowly absorbed from body tissue. As a result of this finding, several protamine-containing commercial proinsulins are available, including protamine zinc insulin (PZI) and NPH insulin. Either of these insulins, upon subcutaneous injection makes available a depot of supply from which insulin is slowly made available and paid out into the body fluids.

Due to the large quantities of protamine-containing insulin formulations that are produced for use by diabetics, it is natural that certain amounts are returned for any of several reasons, including, for example, outdating, lack of refrigeration, and miscellaneous cosmetic defects. It is highly desirable to have a facile and efficient method available for recovering high purity insulin from formulations containing the protamine-insulin complex. Such insulin then could be re-processed and formulated for distribution to diabetics.

An examination of the literature indicates that, although it contains in abundance papers directed to the extraction and purification of insulin from pancreas glands, it fails to address methods for recovering insulin from protamine-insulin complexes. It is to such a method that this invention is directed.

SUMMARY OF THE INVENTION

Therefore, this invention defines a process for recovering insulin from an insulin-protamine complex, which comprises (1) bringing the insulin-protamine complex into contact with an aqueous medium having a pH of from about 2 to about 5 and containing an insulin dissociating or depolymerizing agent, a cation exchanger, and salt at a concentration of from about 0.1 M to about 0.6 M, and (2) recovering insulin having reduced protamine content.

DETAILED DESCRIPTION OF THE INVENTION

As noted, this invention comprises a process for recovering high purity insulin from an insulin-protamine complex. The process permits recovery of insulin at levels representing 90–100% of total insulin with substantially complete removal of the protamine.

In general, the process of this invention involves the use of a cation exchanger. Typical cation exchangers include, for example, SP (sulfopropyl) Sephadex, CM (carboxymethyl) Sephadex, SE (sulfoethyl) cellulose, CM Trisacryl and the like. Of the above, SP Sephadex is preferred.

Essentially, insulin is recovered from insulin-protamine by contact under suitable conditions with the cation exchanger.

Insulin molecules tend to associate forming complexes and polymers, typically as dimers and hexamers. Suitable conditions under which contact with the cation exchanger is effected include, therefore, the use of an aqueous medium containing an agent that exhibits an insulin dissociating or depolymerizing effect. Examples of suitable dissociating and depolymerizing agents are urea; guanidine; lower alkyl alcohols, such as methanol and ethanol; amides, including N,N-dialkylamides such as N,N-dimethylformamides and N,N-dimethylacetamide, acetamide, N-alkylamides such as N-methylacetamide; nitriles, such as acetonitrile, and the like. Any of these are effective in producing monomeric insulin or at least in promoting insulin dissociation. A requirement of the insulin dissociating agent is that it be water soluble or water miscible. Of the foregoing non-exhaustive list of insulin dissociating agents, urea and lower alkyl alcohols are preferred, and urea is most preferred. When a lower alkyl alcohol is used, it preferably is present in an amount, based by volume upon the total medium, of about 30% to about 70%, and, preferably, of about 40% to about 60%. When urea is used, it generally is present in the aqueous medium at a concentration of from about 2 M to about 8 M, preferably from about 5 M to about 8 M, and, most preferably, about 7 M.

In addition to the use of an insulin dissociating or depolymerizing agent, the process of this invention is carried out in an acidic environment at a pH of from about 2 to about 5, preferably from about 3.5 to about 4.5, and at a temperature below about 25° C. and above the freezing point of the aqueous medium. Preferably, the process is carried out with cooling, the temperature being in the range of from about 4° C. to about 8° C. The process generally is run for a period no longer than about 4 hours and usually much less, e.g., for from about 30 minutes to about 1–2 hours.

Any of a wide range of inorganic and organic acids can be used to lower the pH of the mixture to the desired range. Preferred acids are hydrochloric acid, sulfuric acid, and acetic acid, and, of these, hydrochloric acid or a mixture of hydrochloric acid and acetic acid are most preferred.

The process is carried out in the presence of a salt. The salt is dissolved in the aqueous medium at a defined molar concentration. In general, the molar concentration ranges from about 0.1 M to about 0.6 M. The preferred range is from about 0.2 M to about 0.5 M with specific highly preferred ranges being dependent upon the particular cation exchanger that is employed. Thus, for example, when SP Sephadex is used the desirable salt concentration is from about 0.35 M to about 0.5 M. When a salt concentration at the lower end of the range is employed, some insulin loss due to retention on the SP Sephadex may be experienced. Conversely, a salt concentration at the higher end of the range, although achieving greater insulin recovery, may result in the presence of undesirable insulin contaminants. For CM Sephadex, the desired range is from about 0.2 M to about 0.3 M, and for SE cellulose, from about 0.35 M to about 0.5 M. Any of a wide range of inorganic salts can be used; the preferred salt, however, is sodium chloride.

Although the process of this invention can be carried out using a variety of techniques and sequences, the following is typical of the general procedure. The insulin-protamine complex is placed in an acid aqueous medium containing the desired concentration of insulin dissociating or depolymerizing agent. The resulting mixture then is brought into contact with the selected cation exchanger, the appropriate quantity of salt is added, and the resultant mixture is maintained at the desired temperature to permit adsorption by the cation exchanger of protamine and insulin from the insulin-protamine complex with accompanying selective desorption of insulin from the cation exchanger. The protamine-free insulin is readily separated by filtering the supernatant from the cation exchanger and, in accordance with standard techniques, isolating the insulin from the supernate.

EXAMPLE 1

An accumulated return stock slurry (20 liters) of insulin-protamine precipitate was filtered to obtain approximately 5 kg. (wet weight) of solids. To the solids were added 8 liters of a 7 M urea, 0.1 M acetic acid buffer. The pH of the resulting mixture was adjusted to 3.7 by addition of 630 ml. of 10% HCl, and the solids were dissolved by agitation. The filter papers were washed with 2 liters of the urea-acetic acid buffer, and the wash was added to the insulin-protamine solution.

The resulting mixture was filtered through fiberglass to obtain 16.57 liters of filtrate, $OD_{278}=87.0$. (Insulin by radioimmunoassay=1503 U/ml.)

Dry SP Sephadex (1500 grams) was swelled in 30 liters of 7 M urea, 0.1 M acetic acid buffer. Excess buffer was decanted from the swelled SP Sephadex, and the insulin-protamine-containing solution was added to the SP Sephadex, producing a total volume of about 33 liters.

Sodium chloride (965 grams) was added to produce a 0.5 M solution. The pH was adjusted to 3.7 by addition of 130 ml. of 10% HCl. The resulting mixture, maintained at about 5° C., was agitated for 2 hours. The Sephadex then was washed twice with 5 liters of pH 3 water. The washes were added to the filtrate.

The insulin-containing filtrate (29 liters, $OD_{278}=42.0$), containing 752 U/ml. insulin as determined by radioimmunoassay, was diluted with 60 liters of chilled purified water. Ethanol (10 liters) was added, and the pH was adjusted to 5.9 with 300 ml. of 28% ammonium hydroxide. To the mixture then were added 200 ml. of 20% $ZnCl_2$ solution. The mixture was agitated for 2 hours and allowed to stand overnight at about 5° C. Zinc insulin crystals were recovered by filtration. The filtrate (about 90 liters) had an $OD_{278}=3.85$. Radioimmunoassay showed an insulin concentration of 0.1 U/ml.

EXAMPLE 2

Wet insulin-protamine return stock precipitate (27.5 kg.) was dissolved in 47.5 liters of 0.1 N acetic acid-7 M urea buffer. The solution was filtered through a Buchner funnel, and 20 liters of the buffer were added as a wash. The resulting mixture, 96 liters, had an insulin activity of 1493 U/ml.

The above solution and 3.7 kg. of NaCl were added to 20 kg. of swollen SP C-25 Sephadex. The pH of the resulting slurry was adjusted to 3.7 with 10% Hcl, and the mixture was stirred for 2 hours at 5° C. The slurry then was filtered using a 30μ mesh Buchner funnel. Water (50 liters) adjusted to pH 3 was passed through the filter as a wash and added to the filtrate. The resulting filtrate (total volume-158 liters) showed by radioimmunoassay an insulin content of 835 U/ml. The product, free of protamine, represents an overall insulin recovery of 92.0%.

The insulin was crystallized according to standard methods using $ZnC_2$, 274 liters of water, 48 liters of ethyl alcohol, 6.15 liters of glacial acetic acid, and 24.5 liters of 6 N $NH_4OH$ to provide an adjusted pH of 5.9.

EXAMPLE 3

Use of Various Cation Exchangers

Insulin-protamine return stock precipitate (about 150 g.) was dissolved in 600 ml. of 0.1 N acetic acid-7 M urea. The solution was filtered and the pH of the filtrate was adjusted to 3.7. The mixture was divided into 6-100 ml. portions. A 100 ml. portion, assayed by radioimmunoassay, showed a total of 163,200 U insulin (1632 U/ml.), $OD_{278}=82.7$.

To each 100 ml. portion were added 50 g. of a cation exchanger, the desired quantity of NaCl, and 7 M urea to a resulting total volume of 200 ml. The mixture was adjusted to pH 3.7. Using this procedure, the following six samples were prepared:

|   | Cation Exchanger | NaCl, M |
|---|---|---|
| A | CM Sephadex | 0.2 |
| B | CM Sephadex | 0.35 |
| C | CM Sephadex | 0.5 |
| D | SE Cellulose | 0.2 |
| E | SE Cellulose | 0.35 |
| F | SE Cellulose | 0.5 |

Each of the mixtures was stirred at 5° C. for 1.5 hours, and the supernatant then was removed by filtration. Analysis of the resulting filtrates gave the results shown in the table following.

| Sample | Filtrate, ml. | Total Insulin, U Radioimmunoassay | $OD_{278}$ | Insulin Recovery, % by Radioimmunoassay | $OD_{278}$ | Protamine Content |
|---|---|---|---|---|---|---|
| A | 192 | 143,808 | 38.9 | 88.1 | 90.3 | None |
| B | 182 | 139,594 | 40.5 | 85.5 | 89.1 | Trace |
| C | 185 | 153,550 | 42.1 | 94.1 | 94.2 | Minor |
| D | 173 | 97,572 | 20.6 | 59.8 | 43.1 | None |
| E | 170 | 117,130 | 38.8 | 71.8 | 79.8 | None |
| F | 157 | 127,327 | 43.2 | 78.0 | 82.0 | None |

We claim:

1. A process for recovering insulin from an insulin-protamine complex, which comprises (1) bringing the insulin-protamine complex into contact with an aqueous medium having a pH from about 2 to about 5 and containing urea at a concentration of from about 2 M to about 8 M, a cation exchanger selected from the group consisting of SP Sephadex and CM Sephadex, and salt at a concentration of from about 0.1 M to about 0.6 M, and (2) recovering insulin having reduced protamine content.

2. A process of claim 1, in which the salt is sodium chloride and is present at a concentration of from about 0.2 M to about 0.5 M.

3. A process of claim 2, in which the insulin-protamine complex is brought into contact with urea, the cation exchanger, and the salt at a temperature of from about 4° C. to about 8° C.

4. A process of claim 3, in which the insulin dissociating or depolymerizing agent is urea present in the aqueous medium at a concentration of from about 2 M to about 8 M.

5. A process of claim 3, in which the urea is present at a concentration of from about 5 M to about 8 M.

6. A process of claim 5, in which the cation exchanger is SP Sephadex.

7. A process of claim 6, in which the salt is present at a concentration of from about 0.35 M to about 0.5 M.

8. A process of claim 7, in which the pH is from about 3.5 to about 4.5.

9. A process of claim 1, in which insulin is recovered substantially free of protamine.

* * * * *